United States Patent [19]

Terashima et al.

[11] Patent Number: 4,892,961
[45] Date of Patent: Jan. 9, 1990

[54] AMINO ACID DERIVATIVES, AND THEIR PRODUCTION

[75] Inventors: Shiro Terashima, Tokyo; Yoshikazu Kimura; Yoshio Ito, both of Sagamihara; Kunikazu Sakai, Tokyo; Tamejiro Hiyama, Sagamihara, all of Japan

[73] Assignee: Sumitomo Pharmaceuticals Company, Limited, Osaka, Japan

[21] Appl. No.: 889,830

[22] Filed: Jul. 28, 1986

[30] Foreign Application Priority Data

Jul. 31, 1985 [JP] Japan .................................. 60-167808
Nov. 15, 1985 [JP] Japan .................................. 60-257340

[51] Int. Cl.$^4$ .................... C07D 315/00; C07F 7/10
[52] U.S. Cl. ................................ 549/419; 556/418; 562/567
[58] Field of Search ................ 562/567; 556/418; 549/419

[56] References Cited

U.S. PATENT DOCUMENTS

| | | | |
|---|---|---|---|
| 2,774,778 | 12/1956 | Sommer | 556/418 |
| 3,962,319 | 6/1976 | Beche et al. | 562/567 X |
| 4,251,325 | 2/1981 | Souzpe et al. | 562/567 X |
| 4,290,972 | 9/1981 | Yoneta et al. | 562/567 X |
| 4,396,775 | 8/1983 | Ohfune et al. | 556/418 X |
| 4,486,600 | 12/1984 | Kleemann et al. | 562/567 |
| 4,501,919 | 2/1985 | Koch | 562/567 X |
| 4,594,446 | 6/1986 | Ueda et al. | 556/418 X |
| 4,595,751 | 6/1986 | Blanc | 562/567 X |
| 4,599,447 | 7/1986 | Tinti | 562/567 |

Primary Examiner—Paul F. Shaver
Attorney, Agent, or Firm—Birch, Stewart, Kolasch & Birch

[57] ABSTRACT

An amino acid derivative of the formula:

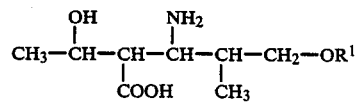

wherein $R^1$ is a protective group for hydroxyl, which is useful as an intermediate for production of antimicrobial agent.

7 Claims, No Drawings

AMINO ACID DERIVATIVES, AND THEIR PRODUCTION

The present invention relates to amino acid derivatives and their production. More particularly, it relates to amino acid derivatives of the formula:

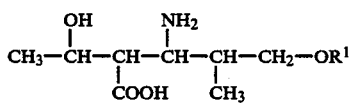

wherein $R^1$ is a protective group for hydroxyl, and their production.

Since the successful isolation of antimicrobial "thienamycin" from nature [U.S. Pat. No. 3,950,357; J. Am. Chem. Soc., 100, 313 (1978)], various carbapenem compounds have been reported. Among them, are carbapenem compounds substituted at the 1-position, and 1β-methylcarbapenem compounds having the following skeleton:

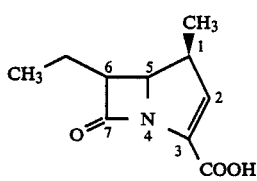

These compounds are particularly notable in exerting strong antimicrobial activity against various microorganisms and have excellent stability in living bodies. In this connection, it is reported that beta-lactam derivatives of the formula:

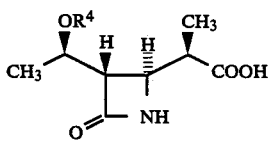

wherein $R^4$ is a hydroxyl protective group are useful as intermediates in the systhesis of said 1β-methylcarbapenem compounds [EP-0071908A; Heterocycles, 21, 29 (1984)].

For production of said beta-lactam derivatives (II) according to the known method as reported, a hydrogen atom at the 1'-position of the acetic acid residue present at the 4-position is withdrawn with a strong base and then a methyl group is introduced therein. However, this method requires disadvantageously carrying out the conversion by the use of lithium diisopropylamide, which can be handled with difficulty, at such a low temperature as $-78°$ C. Further, said method affords unnecessary 1'α-epimers in such an unfavorable proportion of 1'β-epimer/1'α-epimer as being ¼.

As a result of the extensive study to overcome the drawbacks in said known method, it has now been found that such prupose can be attained by production of the beta-lactam derivatives (II) through the amino acid derivatives (I). This invention is based on the above finding.

Accordingly, an object of this invention is to provide the amino acid derivatives having the formula (I). Another object of this invention is to provide a process for preparing the amino acid derivatives (I). A further object of the invention is to provide a process for preparing the beta-lactam derivatives (II) from the amino acid derivatives (I). These and other objects will be apparent to those skilled in the art from the foregoing and subsequent descriptions.

The objective amino acid derivatives represented by the plane formula (I) comprise four asymmetric carbon atoms and have many isomers based thereon. All of those isomers and their mixtures are included in this invention. Among them, the optical isomer of the formula:

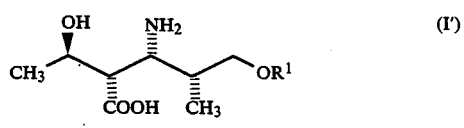

wherein $R^1$ is as defined above is particularly useful, and therefore this invention will be hereinafter explained more in details taking this optical isomer as an example. Needless to say, the conversions adopted for preparation of and use of the optical isomer (I') is equally applicable to isomers.

Still, the protective group for hydroxyl (i.e. the hydroxyl-protective group) may be any one generally employed for protecting a hydroxyl group from its conversion. Likewise, the protective group for amino (i.e. the amino-protective group) and the protective group for carboxyl (i.e. the carboxyl-protective group) may be those as conventionally employed. Specific examples of the hydroxyl-protective group, the amino-protective group and the carboxyl-protective group as well as their introduction and elimination are described, for instance, in "Protective Groups in Organic Synthesis" (1981); published by John Wiley & Sons.

The optically active amino acid derivative (I') can be produced, for instance, according to the following conversions:

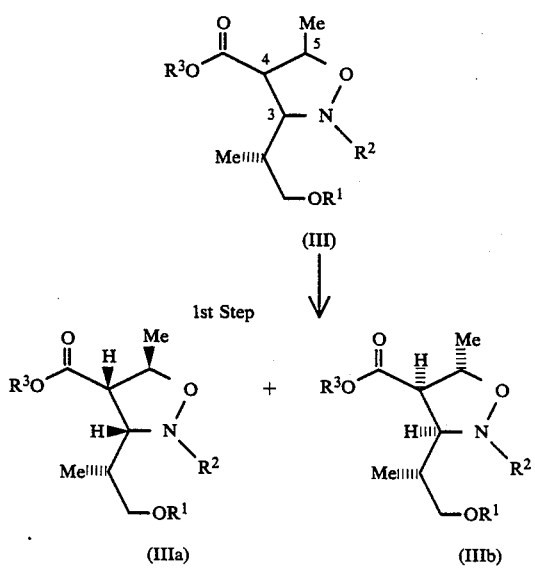

2nd Step

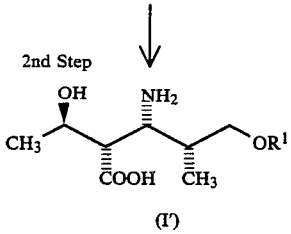

(I')

wherein R¹ is as defined above, R² is a protective group for amino and R³ is a protective group for carboxyl.

Examples of the hydroxyl-protective group are tri(-lower)alkylsilyl (e.g. trimethylsilyl, triethylsilyl, t-butyldimethylsilyl), mono(lower)alkyldiarylsilyl (e.g. t-butyldiphenylsilyl), alkoxy-, alkoxyalkoxy- or aralkoxy-substituted methyl (e.g. methoxymethyl, methylthiomethyl, benzyloxymethyl, t-butoxymethyl, 2-methoxyethoxymethyl), tetrahydropyranyl, substituted or unsubstituted arylmethyl (e.g. benzyl, p-methoxybenzyl, 2,4-dimethoxybenzyl, o-nitrobenzyl, p-nitrobenzyl), substituted or unsubstituted triarylmethyl, (e.g. triphenylmethyl, p-methoxyphenyldiphenylmethyl, bis-(p-methoxyphenyl)-phenylmethyl), acyl (e.g. acetyl, benzoyl), etc.

Examples of the amino-protective group are substituted or unsubstituted phenyl(lower)alkyl (e.g. benzyl, p-methxoybenzyl, 2,4-dimethoxybenzyl, o-nitrobenzyl, p-nitrobenzyl), di(substituted or unsubstituted phenyl)-methyl (e.g. diphenylmethyl, di-p-anisylmethyl), trityl, substitited or unsubstituted phenyl (e.g. p-methoxyphenyl, 2,4-dimethoxyphenyl, o-nitrophenyl, p-nitrophenyl, 2,4-dinitrophenyl), etc. Examples of the carboxyl-protective group are substituted or unsubstituted phenyl(lower)alkyl (e.g. benzyl, p-methoxybenzyl, 2,4-dimethoxybenzyl, o-nitrobenzyl, p-nitrobenzyl, p-chlorobenzyl), lower alkyl (e.g. methyl, ethyl, isopropyl, t-butyl), halo(lower)alkyl (e.g. 2-iodoethyl, 2,2,2-trichloroethyl), lower alkoxy(lower)alkyl (e.g. methoxymethyl, ethoxymethyl, isobutoxymethyl), lower alkoxycarbonyloxy(lower)alkyl (e.g. 1-methoxycarbonyloxyethyl, 1-ethoxycarbonyloxyethyl), lower alkenyl (e.g. allyl, 2-methylallyl, 3-methylallyl), di(substituted or unsubstituted phenyl)methyl (e.g. diphenylmethyl, di-p-anisylmethyl), substituted or unsubstituted phenyl (e.g. phenyl, 4-nitrophenyl, 2,6-dimethylphenyl), etc.

In the above conversions, the first step comprises recovery of two diastereomers from four diastereomers through asymmetric hydrolysis. Namely, the hydrolysis of a mixture of four diastereomers of the oxazolidine derivative (III) results in selective hydrolysis of two diastereomers taking a trans-configuration at the 3- and 4-positions with non-conversion of two other diastereomers taking a cis-configuration at said positions. Thus, a mixture of two 3,4-cis-diastereomers (IIIa) and (IIIb) as non-converted can be recovered from the reaction mixture.

The asymmetric hydrolysis may be carried out by treatment of the mixture of of four diastereomers with a hydrolyzing agent, preferably in an inert solvent.

As the hydrolyzing agent for asymmetric hydrolysis, there are exemplified aqueous solutions of barium hydroxide, sodium hydroxide, potassium hydroxide, tetrabutylammonium hydroxide, etc. Examples of the inert solvent are tetrahydrofuran, acetone, methanol, pyridine, etc. Their mixtures with water are also usable as the inert solvent. The reaction may be effected while cooling or heating, and a preferred temperature is from 0° to 70° C.

Recovery of a mixture of non-hydrolyzed two diastereomers (IIIa) and (IIIb) may be performed by a per se conventional separation procedure, for instance, extracting the reaction mixture with an organic solvent, washing the extract with water, drying the washed extract and evaporation of the organic solvent from the extract. As the organic solvents for extraction, there may be used aromatic hydrocarbons (e.g. n-hexane, benzene, toluene), halogenated hydrocarbons (e.g. chloroform, dichloromethane), esters (e.g. ethyl acetate), ethers (e.g. diethyl ether), etc.

The second step comprises hydrogenation of the diastereomers (IIIa) and (IIIb) for cleavage of the nitrogen-oxygen bond, followed by elimination of the amino-protective group and the carboxyl-protective group to give the optically active amino acid derivative (I').

Hydrogenation may be carried out by catalytic hydrogenation, e.g. by treatment of a mixture of the diastereomers (IIIa) and (IIIb) with hydrogen in the presence of a hydrogenation catalyst such as palladium-carbon, platinum oxide, rhodium-carbon or platinum hyroxide, usually under a hydrogen pressure of 1 to 10 atm. The hydrogenation is preferably effected in an inert solvent, of which typical examples are methanol, ethanol, acetic acid and tetrahydrofuran, and their mixtures. The reaction may be controlled or accelerated by cooling or heating.

Elimination of the amino-protective group and the carboxyl-protective group may be accomplished simultaneously or in order. As the procedure for elimination, there may be adopted any conventional one depending upon the kind of protective group. For instance, in the case of the amino-protective group being a substituted or unsubstituted phenyl(lower)alkyl group or a di(substituted or unsubstituted phenyl)methyl group, reduction or treatment with an acid can accomplish the elimination. The reduction may be carried out by catalytic reduction using a catalyst such as platinum or palladium-carbon. The acid treatment may be performed by contacting with an acid such as a mineral acid or a Lewis acid, especially trifluoracetic acid, boron trifluoride, boron tribromide, aluminum trichloride or the like, optionally in an inert solvent (e.g. dichloromethane, chloroform, benzene, toluene). Further, for instance, a lower alkyl group as the carboxyl-protective group may be eliminated by hydrolysis with an alkali; a halo(lower)alkyl group can be eliminated by reduction with zinc in an organic solvent (e.g. acetic acid, tetrahydrofuran, methanol); a lower alkoxy(lower)alkyl group is eliminated by treatment with an acid (e.g. hydrochloric acid, sulfuric acid, acetic acid, trifluoracetic acid); a substituted or unsubstituted phenyl(lower)alkyl group can be eliminated by the same procedure as hereinabove stated for elimination of the amino-protective group.

The thus produced optically active amino acid derivative (I'), which may be used without separation from the reaction mixture or after separation from the reaction mixture, can be converted into the beta-lactam derivative (II) by subjecting the former to cyclization to give the beta-lactam derivative (IX) [cf. Tetrahedron Letters, 21, 2783–2786 (1980); J. Am. Chem. Soc. 103, 2405–2406 (1981)] and, after protection of the hydroxyl group in the side chain at the 3-position and elimination of the hydroxyl-protective group in the side chain at the 4-position, subjecting the resultant product to oxidation to give the beta-lactam derivative (II) [cf. J. Am. Chem. Soc., 105, 1659–1660 (1983)]. These conversions are representable by the following formulas:

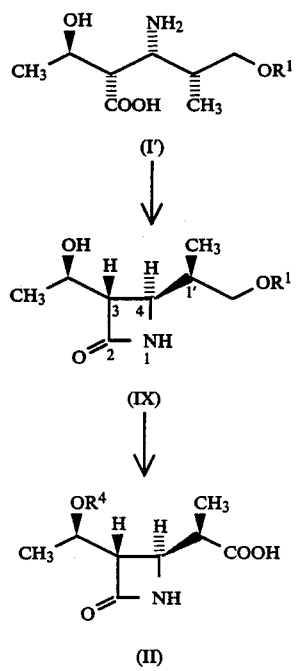

wherein R¹ and R⁴ are each as defined above.

The oxazolidine derivative (III) as the starting material in the process of this invention may be produced by various procedures, of which a typical example is representable by the following formulas:

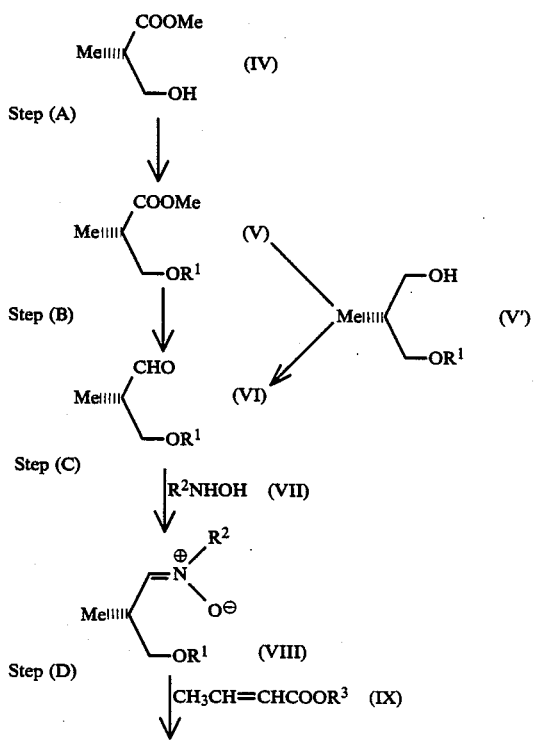

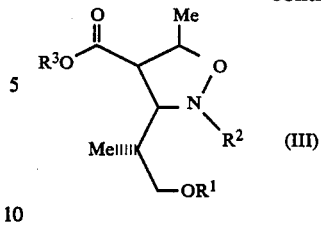

wherein $R^1$, $R^2$ and $R^3$ are each as defined above.

Explaining the above conversions, the step (A) comprises protection of the hydroxyl group in optically active methyl (S)-(+)-3-hydroxy-2-methylpropionate (IV) to give methyl (S)-(+)-3-protected hydroxy-2-methylpropionate (V). This protection may be achieved by a per se conventional procedure for protection of a hydroxyl group, for instance, reacting the compound (IV) with a chloride such as a tri(lower)alkylsilyl chloride, a lower alkoxy- or ar-(lower)alkoxy-substituted methyl chloride, a substituted or unsubstituted monoarylmethyl chloride or a triarylmethyl chloride in the presence of a base such as an organic base (e.g. triethylamine, diisopropylethylamine, imidazole, pyridine) or an alkali metal hydride (e.g. sodium hydride) in an inert solvent such as an ether (e.g. ether, tetrahydrofuran, dimethoxyethane), a halogenated hydrocarbon (e.g. chloroform, dichloromethane), acetonitrile or dimethylformamide.

The step (B) comprises conversion of the ester (V) to give the corresponding aldehyde (VI). This conversion may be accomplished in a single step, i.e. by reduction of the ester (V) with a reducing agent such as diisobutylaluminum hydride at a temperature below about −60° C., or in two steps, i.e. by reduction of the ester (V) with a reducing agent such as lithium aluminum hydride, sodium borohydride or diisobutylaluminum hydride and oxidation of the resulting alcohol (V') by the use of an oxidizing agent such as pyridinium chlorochromate, pyridinium dichromate, dimethylsulfoxide or manganese dioxide. The two step conversion is advantageous in that the reactions therein may be effected at room temperature.

The step (C) comprises reaction of the aldehyde (VI) with the protected hydroxylamine (VII) to give the corresponding nitrone (VIII). The protected hydroxylamine (VII) can be readily synthesized from the corresponding oxime [J. Am. Chem. Soc., 93, 2897 (1971)]. The reaction is usually carried out by treatment of the aldehyde (VI) with the protected hydroxylamine (VII) in the presence of a dehydrating agent (e.g. calcium chloride, molecular sieve) in an inert solvent (e.g. benzene, toluene, ether, tetrahydrofuran, dioxane) at a temperature of 0° C. to room temperature.

The step (D) comprises reaction of the nitrone (VIII) with crotonic acid or its ester (IX) to give the oxazolidine derivative (III). This reaction is normally effected by treatment of the nitron (VIII) with crotonic acid or its ester (IX) in an inert solvent (e.g. benzene, toluene, xylene, ether, tetrahydrofuran, dioxane, dimethylformamide, dimethylsulfoxide) at a temperature of 0° to 100° C.

In place of the steps (C) and (D), the direct conversion of the aldehyde (VI) into the oxazolidine derivative (III) may be achieved by reacting the aldehyde (VI) with the protected hydroxylamine (VII) in the presence of the crotonic acid ester (IX). This reaction is normally effected in an inert solvent as exemplified above at a temperature of 0° to 100° C.

Practical and presently preferred embodiments of the invention are illustratively shown in the following examples wherein the abbreviations indicate the following meanings:

TBDMS: t-butyldimethylsilyl group
Z: benzyloxycarbonyl group
THP: tetrahydropyranyl group
Bu: n-butyl group
Ph: phenyl group
Me: methyl group
TLC: thin layer chromatography

REFERENCE EXAMPLE 1-1

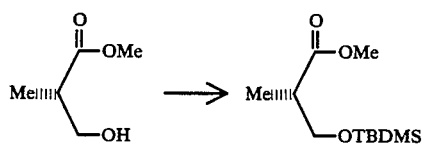

A mixture of methyl (S)-(+)-3-hydroxy-2-methylpropionate (1.00 g; 8.47 mmol) and imidazole (1.15 g; 16.9 mmol) was dissolved in anhydrous dimethylformamide (10 ml), and t-butyl-dimethylchlorosilane (1.30 g; 8.62 mmol) was added thereto at room temperature, followed by stirring at room temperature for 1.5 hours. To the reaction mixture, water (10 ml) and hexane (20 ml) were added, and after separation of the organic layer, the aqueous layer was extracted with hexane (10 ml) two times. The organic layers were combined together, washed with water (5 ml) three times and dried over anhydrous magnesium sulfate. Removal of the solvent by distillation under reduced pressure gave methyl (S)-(+)-3-(t-butyldimethylsilyloxy)-2-methylpropionate (1.91 g; yield, 97%) as a colorless oil. A portion of the oil (179 mg) was distilled by Kugelrohr ® to give a purified product (176 mg) (bath temperature: 120° C./14 mmHg).

$[\alpha]_D^{20}$: +18.9° (c=1.00 , CHCl$_3$).
IR (neat): 1740 cm$^{-1}$.
Mass m/e: 175 (M-Bu)$^+$.
$^1$H NMR δ (CDCl$_3$): 0.03 (6H, s), 0.87 (9H, s), 1.13 (3H, d, J=7 Hz), 2.64 (1H, q, J=7 Hz), 3.66 (3H, s).

REFERENCE EXAMPLE 1-2

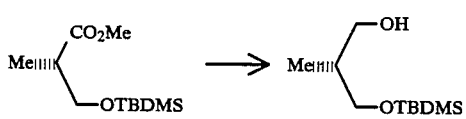

Methyl (S)-(+)-3-(t-butyldimethylsilyloxy)-2-methylpropionate (10.0 g; 43.1 mmol) was dissolved in anhydrous dichloromethane (100 ml), and a hexane solution (100 ml) of 1M diisobutylaluminum hydride was dropwise added thereto at a temperature below 0° C. in an argon stream. After stirring for 30 minutes, water (20 ml) was added thereto, and the resultant mixture was stirred for 1 hour, followed by separation of the organic layer. The aqueous layer was extracted with dichloromethane, and the extracts were combined together with the organic layer. The solvent was distilled under reduced pressure to give (R)-(+)-3-(t-butyldimethylsilyloxy)-2-methyl-1-propanol (7.9 g; yield, 90%) as a colorless oil. A portion of the oil was distilled to give a purified product (bath temperature: 112° C./17 mmHg).

$[\alpha]_D^{20}$: +10.2° (c=1.70, CHCl$_3$).
IR (neat: 1470, 1252 cm$^{-1}$.
Mass m/e: 147 (M-Bu)$^+$.
$^1$H NMR δ (CDCl$_3$): 0.04 (6H, s), 0.81 (3H, d, J=7.0 Hz), 0.87 (9H, s), 1.90 (1H, m), 2.70 (1H, bt, J=5.7 Hz).

REFERENCE EXAMPLE 1-3

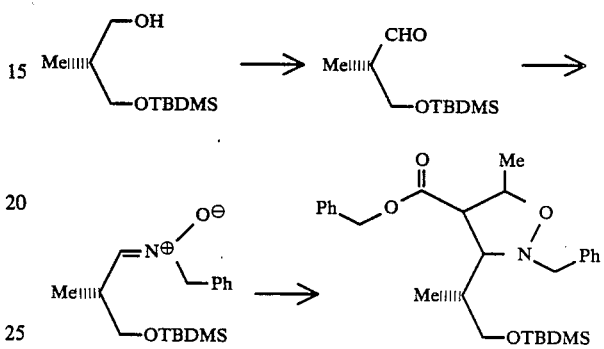

(1) (R)-(+)-3-(t-Butyldimethylsilyloxy)-2-methyl-1-propanol (3.0 g; 14.7 mmol) was added to a mixture of dimethylsulfoxide (20 ml) and triethylamine (13.4 ml), and a solution of the pyridine complex of sulfur trioxide (6.9 g; 43.3 mmol) in dimethylsulfoxide (20 ml) was added thereto at a temperature below 20° C. under stirring. Stirring was continued for 10 minutes, and an aqueous solution (80 ml) of 2M potassium dihydrogenphosphate and ice (40 g) were added thereto to stop the reaction. Insoluble materials were removed by filtration, and the filtrate was extracted with hexane (100 ml) three times. The organic layer was washed successively with water and aqueous sodium chloride and dried over anhydrous sodium sulfate. Removal of the solvent by distillation under reduced pressure gave (S)-(+)-3-(t-butyldimethylsilyloxy)-2-methylpropanal (2.46 g; yield, 81%) as a colorless oil. The NMR spectrum of this product was identical to that of the product as obtained in Reference Example 2-1.

(2) (S)-(+)-3-(t-Butyldimethylsilyloxy)-2-methylpropanal (2.46 g; 12.2 mmol) as above obtained was dissovled in benzyl crotonate (8.20 g; 46.6 mmol), and benzylhydroxylamine (1.43 g; 11.6 mmol) was added thereto with ice-cooling and followed by stirring. Water was removed under reduced pressure (1 mmHg), and the resulting mixture was stirred at 80° C. for 12 hours. Excess benzyl crotonate was removed by distillation at 110° C. under reduced pressure to give crude 2-benzyl-4-benzyloxycarbonyl-3-[(2'-t-butyldimethylsilyloxy-1'-methyl)ethyl]-5-methylisoxazolidine (5.5 g) as a mixture of four diastereomers.

IR (neat): 1738 cm$^-$.
Mass m/e: 483 (M$^{30}$).
$^1$H NMR δ (CDCl$_3$): 0.00–0.05 (6H), 0.88 (9H), 1.35 (3H, bd, J=6.0 Hz), 5.21–5.24 (2H), 7.30–7.41 (10H).

EXAMPLE 1-1

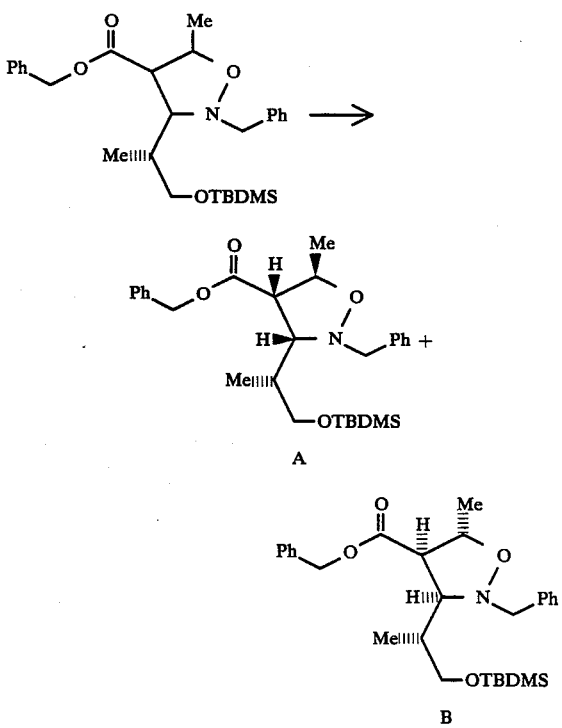

A mixture (5.5 g) of four diastereomers 2-benzyl-4-benzyloxycarbonyl-3-[(2'-t-butyldimethylsilyloxy-1'-methyl)ethyl]-5-methylisoxazolidine as obtained in Reference Example 1-3 was dissolved in tetrahydrofuran (50 ml). The resultant solution was added to a saturated aqueous solution of barium hydroxide (50 ml) and followed by vigorous stirring for 24 hours. Insoluble materials were removed by filtration, and the filtrate was added to hexane (150 ml) to extract. The extract was washed with a saturated aqueous solution of sodium hydrogencarbonate (10 ml) and then a saturated aqueous solution of sodium chloride (20 ml) two times, dried over anhydrous sodium sulfate and followed by removal of the solvent. The oily residue was purified by silica gel column chromatography using a mixture of hexane and ethyl acetate (100:0–95:5) to give a mixture (3.0 g) of 3,4-cis diastereomers (A and B) of 2-benzyl-4-benzyloxycarbonyl-3-[(2'-t-butyldimethylsilyloxy-1'-methyl)ethyl]-5-methylisoxazolidine.

The proportion of the diastereomers A and B was confimed to be 13:9 by NMR spectrum.

EXAMPLE 1-2

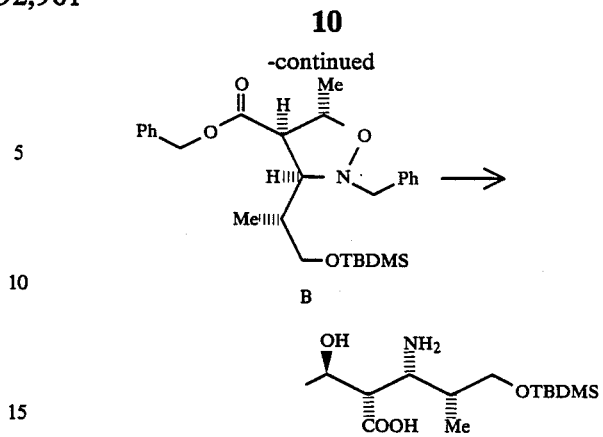

A mixture of two diastereomers (A and B) of 2-benzyl-4-benzyloxycarbonyl-3-[(2'-t-butyldimethylsilyloxy-1'-methyl)ethyl]-5-methylisoxazolidine as obtained in Example 1-1 (10.0 g; 20.7 mmol) was dissolved in methanol (50 ml), and 10% palladium-carbon (1 g) was added thereto, followed by stirring under a pressure of 5 atm in hydrogen atmosphere for 7 hours. The reaction mixture was filtered upon celite to remove the catalyst, and the solvent was distilled under reduced pressure. Purification of the residue by silica gel column chromatography using a mixture of chloroform and methanol (10.1:–8:1) gave (2S,3R,4R)-3-amino-5-t-butyldimethylsilyloxy-2-[(1'R)-(1'-hydroxyethyl)]-4-methylpentanoic acid (1.30 g; yiled, 21%) as a colorless solid from a fraction having a stronger polarity. Recrystallization from a mixture of ethanol and water (1:2) gave colorless needles. M.P., 178°–179° C. (decomp.).

$[\alpha]_D^{20}$: −2.0° (c=1.18, MeOH).

IR (KBr): 1340, 1405, 1480, 1540, 1640, 2120, 2900, 3500 cm$^{-1}$.

Mass m/e: 290 (M-NH$_3$)$^+$, 270(M-COOH)$^+$, 248 (M-Bu)$^+$.

$^1$H NMR δ (CDCl$_3$): 0.06 (6H, s), 0.89 (9H, s), 1.12 (3H, d, J=7.0 Hz), 1.23 (3H, d, J=6.4 Hz), 1.95 (1H, m), 2.51 (1H, m), 3.69 (3H, m), 4.21 (1H, m).

Elementary analysis for C$_{14}$H$_{31}$O$_4$NSi: Calcd.: C, 55.04%; H, 10.23%; N, 4.59%. Found: C, 54.81%; H, 10.26%; N, 4.48%.

REFERENCE EXAMPLE 2-1

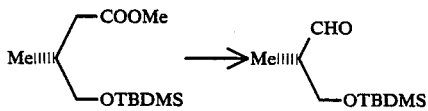

Methyl (S)-(+)-3-(t-butyldimethylsilyloxy)-2-methylpropionate (1.31 g; 5.6 mmol) was dissolved in anhydrous ether (18.5 ml), and a hexane solution (8.4 ml) of 1M diisobutylaluminum hydride was added dropwise thereto at −78° C. in 5 minutes in an argon stream. After stirring for 30 minutes, methanol (0.09 ml) and then water (0.84 ml) were added thereto, and the resultant mixture was allowed to stand at room temperature, followed by stirring at the same temperature for 1 hour. The reaction mixture in gel was filtered, dried over anhydrous magnesium sulfate, and the solvent was distilled under reduced pressure. Purification of the oily residue by silica gel column chromatography using a mixture of hexane and ethyl acetate (9:1) gave (S)-(+)-

3-(t-butyldimethylsilyloxy)-2-methylpropanal (0.89 g, yield, 78%) as a colorless oil.

$[\alpha]_D^{20}$: +37.8° (c=1.20, CHCl$_3$).

IR (neat): 1735 cm$^{-1}$.

$^1$H NMR δ (CDCl$_3$): 0.06 (6H, s), 0.88 (1 H, s), 1.09 (3H, d, J=7 Hz), 2.57 (1H, tq, J=7 Hz and 6 Hz), 3.84 (2H, d, J=6 Hz), 9.74 (1H, d, J=1.5 Hz).

REFERENCE EXAMPLE 2-2

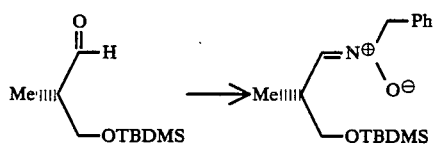

To a mixture of N-benzylhydroxylamine prepared by the method as described in J. Am. Chem. Soc., 93, 2897 (1971) (368 mg; 3.0 mmol) and calcium chloride (3.30 mg; 3.0 mmol), anhydrous ether (30 ml) was added in argon stream, and (S)-(+)-3-(t-butyldimethylsilyloxy)-2-methylpropanal (600 mg; 3.0 mmol) was added dropwise thereto at 0° C. Stirring was continued at the same temperature for 1 hour and then at room temperature for 2 hours. The reaction mixture was filtered, and the filtrate was distilled under reduced pressure to remove the solvent. The oily residue was purified by silica gel column chromatography using a mixture of hexane and ethyl acetate (5:5–0:10) to give (R)-(−)-N-(3-t-butyl-dimethylsilyloxy-2-methylpropylidene)benzylamine-N-oxide (658 mg; 64%).

$[\alpha]_D^{20}$: −37.7° (c=0.89, CHCl$_3$).

IR (neat): 1595 cm$^{-1}$.

Mass m/s: 307 (M+).

Elementary analysis for C$_{17}$H$_{29}$O$_2$NSi: Calcd.: C, 66.40%; H, 9.51%; N, 4.55%. Found: C, 65.86%; H, 9.25%; N, 4.46%.

$^1$H NMR δ (CDCl$_3$): ~0.02 (3H, s), 0.00 (3H, s), 0.84 (9H, s), 1.10 (3H, d, J=7 Hz), 3.10–3.40 (1H, bm), 3.63 (2H, t, J=5 Hz), 4.87 (2H, s), 6.59 (1H, d, J=7 Hz), 7.37 (5H, s).

REFERENCE EXAMPLE 2-3

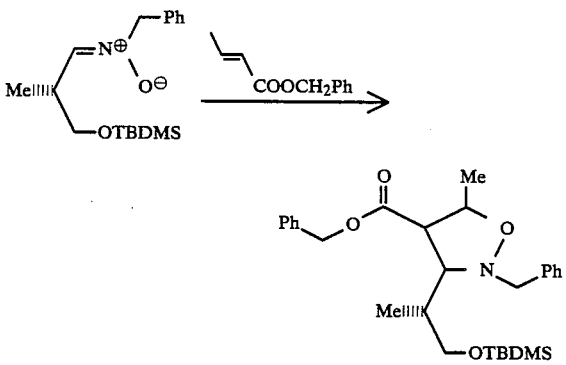

To a solution of (R)-(−)-N-(3-t-butyldimethyl-silyloxy-2-methyl-1-propylidene)benzylamine-N-oxide (469 mg; 1.53 mmol) in anhydrous toluene (5 ml), there was added benzyl crotonate (1.08 g; 6.14 mmol), and stirring was made at 80° C. for 10 hours. The solvent and excess benzyl crotonate were removed by distillation at 120° C. under 1 Torr. The oily residue was purified by silica gel chromatography using a mixture of hexane and ethyl acetate (95:5) to give 2-benzyl-4-ben- zyloxycarbonyl-3-[(2'-t-butyldimethylsilyloxy-1'-methyl)ethyl]-5-methylisoxazolidine (443 mg; yield, 60%) as a colorless oil.

IR: 1738 cm$^{-1}$.

Mass m/e: 483 (M$^{30}$).

$^1$H NMR δ (CDCl$_3$): 0.00–0.05 (6H, s), 0.88 (9H, s), 1.35 (3H, bd), 5.21–5.24 (2H, s), 7.30–7.41 (10H, s).

EXAMPLE 2

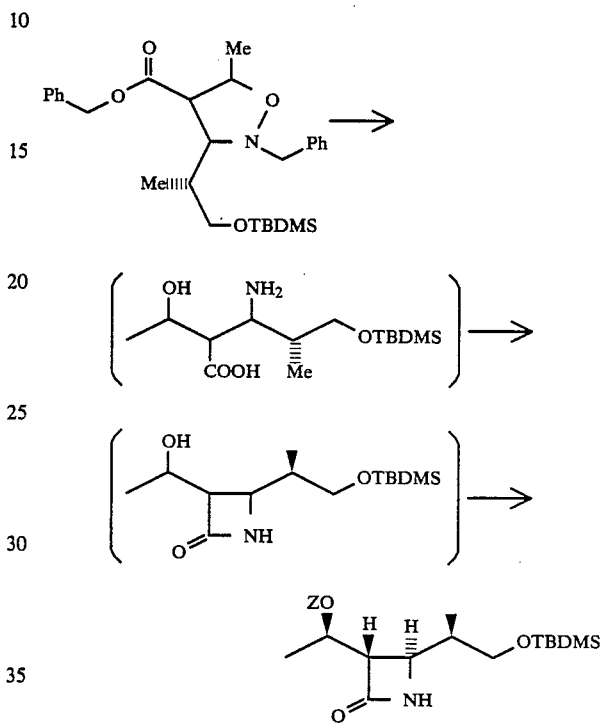

(1) 2-Benzyl-4-benzyloxycarbonyl-3-[(2'-t-butyldime-thylsilyloxy-1'-methyl)ethyl]-5-methylisoxazolidine (175 mg; 0.36 mmol) as obtained in Reference Example 2-3 was dissolved in methanol (3.6 ml), and 10% palladium-carbon (52 mg) was added thereto, followed by stirring for 40 hours under a pressure of 5 atm in hydrogen atmosphere. The reaction mixture was filtered upon celite to remove the catalyst, and the solvent was distilled under reduced pressure to give 3-amino-5-t-butyl-dimethylsilyloxy-2-(1'-hydroxyethyl)-4-methylpentanoic acid (110 mg).

(2) The thus obtained 3-amino-5-t-butyldimethyl-silyloxy-2-(1'-hydroxyethyl)-4-methylpentanoic acid (110 mg) was dissolved in anhydrous acetonitrile (30 ml) and combined with 2,2'-dipyridyldisulfide (91 mg; 0.41 mmol), followed by heating under reflux. A solution of triphenylphophine (110 mg; 0.42 mmol) in anhydrous acetonitrile (6.2 ml) was gradually added thereto, and heating under reflux was continued for 3 hours. After cooling to room temperature, the solvent was distilled under reduced pressure. The produced substance was separated into two fractions by TLC.

(3) The substance obtained from the fraction having a stronger polarity (21.0 mg; 0.073 mmol) was dissolved in anhydrous dichloromethane (1 ml), and p-dime-thylaminopyridine (26 mg; 0.21 mmol) and benzyl chloroformate (30 ml; 0.21 mmol) were added thereto with ice-cooling, and the resultant mixture was stirred at room temperataure for 1 hour. p-Dimethylaminopyridine (26 mg; 0.21 mmol) and benzyl chloroformate (30 ml; 0.21 mmol) were again added thereto, followed by stirring for 1 hour. The solvent was distilled under reduced pressure, and the residue was purified by TLC using a mixture of hexane and ethyl acetate (8:2) to give (3S,4R)-3-[(1'R)-1'-(benzyloxycarbonyloxy)ethyl]-4-[(1'R)-1'-(t-butyldimethylsilyloxymethyl)ethyl]azetidin-2-one (24.9 mg; yield, 16.4%). Specific rotation and spectra of IR, NMR and Mass were identical to those of the product as obtained in Reference Example 5-2.

REFERENCE EXAMPLE 3

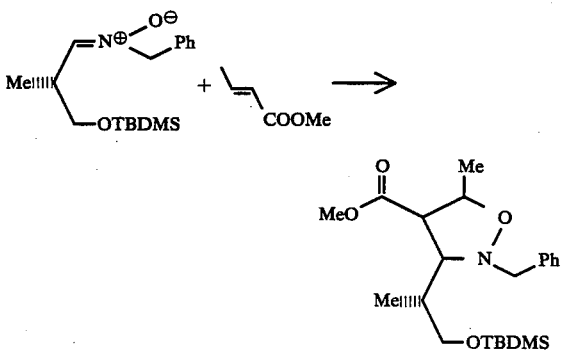

(R)-(−)-N-(3-t-butyldimethylsilyloxy)-2-methyl-1-propylidene)-benzylamine-N-oxide (658 mg; 2.14 mmol) was dissolved in anhydrous toluene (2.1 ml), and methyl crotonate (2.28 ml; 21.4 mmol) was added thereto, followed by stirring at 80° C. for 10 hours. The solvent and excess methyl crotonate were removed by distillation under reduced pressure, and the oily residue was purified by silica gel column chromatogtaphy using a mixture of hexane and ethyl acetate (9:1) to give 2-benzyl-3-[(2-t-butyl-dimethylsilyloxy-1'-methyl)ethyl]-4-methoxycarbonyl-5-methylisoxazolidine (654 mg; yield, 75%) as a mixture of four diastereomers.

IR (KBr): 1740 cm$^{-1}$.

Mass m/e: 407 (M+).

$^1$H NMR δ (CDCl$_3$): ∼0.02–0.03 (6H, s), 0.86 (9H, s), 0.97 (3H, d), 1.30–1.40 (3H, d), 3.73, 3.72, 3.76, 3.78 (total 3H, four s), 7.32 (5H, s).

EXAMPLE 3

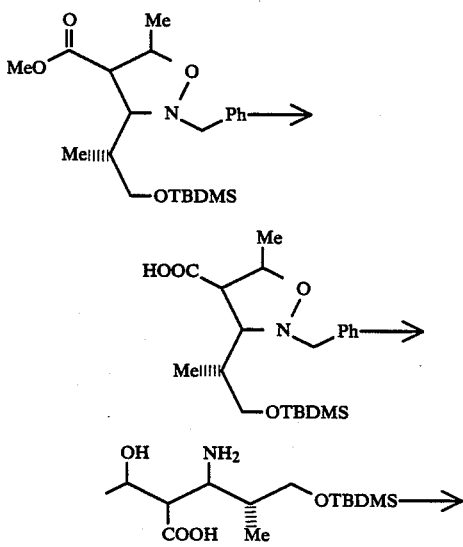

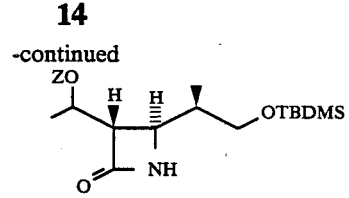

(1) To a mixture (117 mg) of four diastereomers of 2-benzyl-3-[(2'-t-butyldimethylsilyloxy-1'-methyl)ethyl)-4-methoxycarbonyl-5-methylisoxazolidine (117 mg; 0.29 mmol) as obtained in Reference Example 3 was added a methanolic solution of 1M potassium hydroxide (1.3 ml), and the resultant solution was stirred at 60° C. for 3 hours, followed by addition of 1M hydrochloric acid solution (1.3 ml) and dichloromethane (3 ml) at room temperature. After separation of the organic layer, the aqueous layer was extracted with dichloromethane. The extracats were combined together with the organic layer and dried over anhydrous sodium sulfate. The solvent was distilled under reduced pressure to give 2-benzyl-3-[(2'-t-butyldimethylsilyloxy-1'-methyl)ethyl]-4-carboxy-5-methylisoxazolidine (102.5 mg; yield, 91%).

(2) 2-Benzyl-3-[(2'-t-butyldimethylsilyloxy-1'-methyl)ethyl]-4-carboxy-5-methylisoxazolidine (102.5 mg) thus obtained was dissolved in methanol (4 ml), followed by addition of 10% palladium-carbon (60 mg) thereto. The resultant mixture was allowed to react for 40 hours under a hydrogen pressure of 5 atm. Subsequent treatment as in Example 2 gave (3S,4R)-3-[(1'R)-1'-(benzyloxycarbonyloxy)ethyl]-4-[(1'R)-1'-(t-butyldimethylsilyloxymethyl)ethyl]-azetidin-2-one (19.2 mg). [α]$_D^{25}$ +10.1° (c=1.08, CHCl$_3$).

IR, NMR and Mass spectra of this product were identical to those of the product as obtained in Reference Example 5-2.

REFERENCE EXAMPLE 4-1

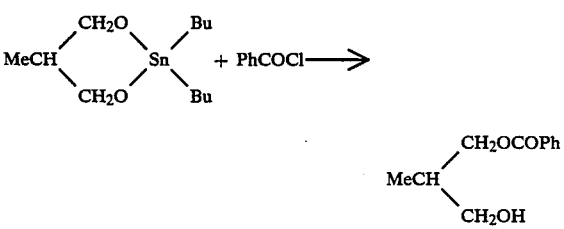

To a solution of 2,2-dibutyl-5-methyl-2-stanna-1,3-dioxane (1.47 g; 4.57 mmol) in anhydrous chloroform (30 ml) was added banzoyl chloride (643 mg; 4.57 mmol), heated under reflux for 1 hour and followed by addition of dioxane (5 ml) containing 10% of water thereto. Heating under reflux was continued for further 1 hour. After cooling, the reaction mixture was successively washed with a saturated aqueous solution of sodium chloride, a saturated aqueous solution of sodium hydrogencarbonate and a saturated aqueous solution of sodium chloride and dried over anhydrous magnesium sulfate. The solvent was distilled under reduced pressurse, and the residue was purified by TLC using a mixture of ethyl acetate and benzene (1:3) to give 3-benzoyloxy-2-methylpropanol (741 mg; yield, 84%).

$^1$H NMR δ (CDCl$_3$): 1.07 (3H, d, J=6 Hz), 1.6–2.2 (2H, m), 3.36–3.62 (2H, m), 4.20–4.32 (2H, m), 7.25–7.55 (3H, m), 7.90–8.13 (2H, m).

REFERENCE EXAMPLE 4-2

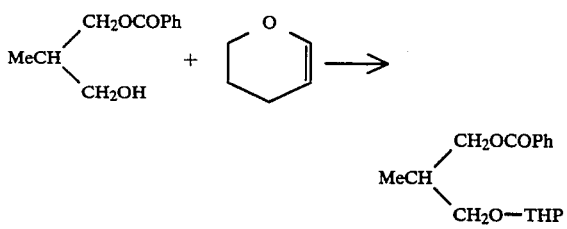

A mixture of 3-benzoyloxy-2-methylpropanol (369 mg; 1.9 mmol), dihydropyran (273 mg; 3.25 mmol) and pyridinium p-toluenesulfonate (50 mg; 0.2 mmol) in anhydrous dichloromethane (10 ml) was stirred at room temperature for 2 hours. Dihydropyran (200 mg; 2.38 mmol) and pyridinium p-toluenesulfonate (50 mg; 0.2 mmol) were further added thereto, and the resultant mixture was stirred for 3 hours. Ether (50 ml) was added to the reaction mixture, which was washed with an aqueous solution of sodium chloride and dried over anhydrous magnesium sulfate. The solvent was removed by distillation, and the residue was purified by TLC using a mixture of ethyl acetate and benzene (1:4) to give 1-benzoyloxy-2-methyl-3-tetrahydropyranyloxypropane (466.3 mg; yield, 88%).

$^1$H NMR δ (CDCl$_3$): 1.07 (3H, d, J=6 Hz), 1.4–1.8 (6H, m), 2.00–2.55 (1H, m), 3.30–3.65 (1H, m), 3.70–3.95 (1H, m), 4.26–4.43 (2H, m), 4.63 (1H, brs), 7.35–7.65 (3H, m), 7.96–8.17 (2H, m).

REFERENCE EXAMPLE 4-3

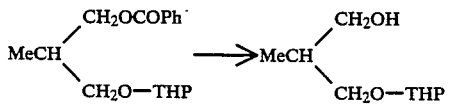

1-Benzoyloxy-2-methyl-3-tetrahydropyranyloxypropane (460 mg; 1.65 mmol) was dissolved in methanol (10 ml), and 1M sodium hydroxide solution (3 ml) and water (10 ml) were added thereto, and the resultant mixture was stirred at room temperature for 5 hours. The reaction mixture was extracted with ethyl acetate. The extracts were washed with water and dried over anhydrous magnesium sulfate. The solvent was removed by distillation, and the residue was purified by silica gel column chromatography using a mixture of ethyl acetate and benzene (1:4) to give 2-methyl-3-tetrahydropyranyloxy-1-propanol (254 mg; yield, 88%).

$^1$H NMR δ (CDCl$_3$): 0.90 (3H, d, J=6 Hz), 1.3–2.3 (7H, m), 2.56 (1H, brs), 3.2–4.1 (6H, m), 4.60 (1H, brs).

REFERENCE EXAMPLE 4-4

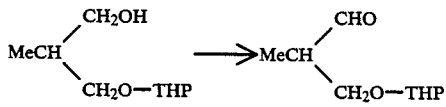

A solution of 2-methyl-3-tetrahydropyranyloxy-1-propanol (250 mg; 1.4 mmol) in dichloromethane (4 ml) was added to a suspension of pyridinium chlorochromate (500 mg; 2.32 mmol) and celite (2.5 g) in dichloromethane (10 ml), and stirred at room temperature for 3 hours. Ether (100 ml) was added thereto. The resultant mixture was filtered, and the filtrate was distilled under reduced pressure to give the solvent. The residue was purified by silica gel chromatography using a mixture of ethyl acetate and benzene (1:4) to give 2-methyl-3-tetrahydropyranyloxypropanal (178 mg; yield, 73%).

$^1$H NMR δ (CDCl$_3$): 1.13 (3H, d, J=6 Hz), 1.40–1.85 (6H, m), 2.45–2.90 (1H, m), 3.40–4.13 (4H, m), 4.62 (1H, brs), 9.75 (1H, d, J=1.0 Hz).

REFERENCE EXAMPLE 4-5

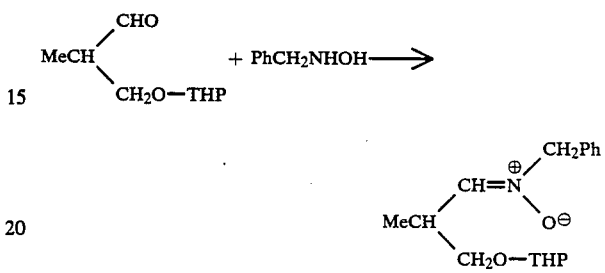

An ethereal solution (1 ml) of 2-methyl-3-tetrahydropyranyloxypropanal (37.9 mg; 0.20 mmol) was added dropwise to a suspension of benzylhydroxylamine (28.7 mg; 0.23 mmol) and powdery calcium chloride (22.2 mg; 0.20 mmol) in ether (0.5 ml) at 0° C., and the resultant mixture was stirred for 1.5 hours. The reaction mixture was purified by TLC using ethyl acetate to give N-(2-methyl-3-tetrahydropyranyloxypropylidene)-benzylamine-N-oxide (34.9 mg; yield, 57%).

$^1$H NMR δ (CDCl$_3$): 1.15 (3H, d, J=6Hz), 1.35–1.80 (6H, m), 3.25–3.90 (5H, m), 4.55 (1H, brs), 4.90 (2H, s), 6.67 (1H, d, J=6 Hz), 7.40 (5H, s).

REFERENCE EXAMPLE 4-6

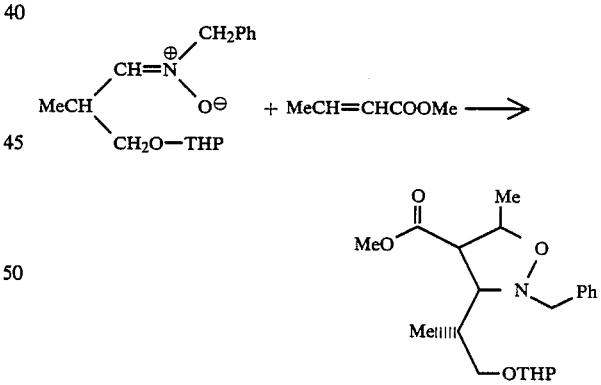

A mixture of N-(2-methyl-3-tetrahydropyranyloxypropylidene)-benzylamine-N-oxide (135 mg; 0.49 mmol), methyl crotonate (490 mg; 4.9 mmol) and toluene (5 ml) was stirred at 105° C. for 3.5 hours. After removal of the solvent and excess methyl crotonate under reduced pressure, the residue was purified by silica gel column chromatography using a mixture of ethyl acetate and benzene (1:4) to give 2-benzyl-3-[(1'-methyl-2'-tetrahydropyranyloxy)ethyl]-4-methoxycarbonyl-5-methylisoxazolidine (107 mg; yield, 58%).

IR: 1740 cm$^{-1}$.

Mass m/e: 378 (M+).

EXAMPLE 4

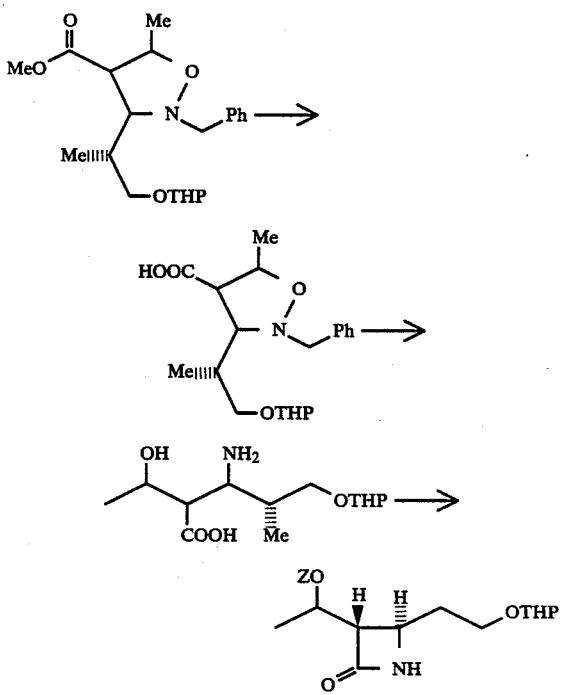

2-Benzyl-3-[(1'-methyl-2'-tetrahydropyranyloxy)ethyl]-4-methoxycarbonyl-5-methylisoxazolidine as obtained in Reference Example 4-6 was treated as in Example 3 to give (3S,4R)-3-[(1'R)-1-benzyloxycarbonyloxy)ethyl]-4-[(1'R)-1'-tetrahydropyranyloxymethyl)ethyl]azetidin-2-one.

IR: 1752 cm$^{-1}$.

Mass m/e: 391 (M+).

$^1$H NMR δ (CDCl$_3$): 0.96–1.00 (3H, d, J=6.8 Hz), 1.43 (3H, d, J=6.4 Hz), 4.50 (1H, brs), 5.14 (2H, s), 5.93 (1H, brs), 7.35 (5H, s).

REFERENCE EXAMPLE 5-1

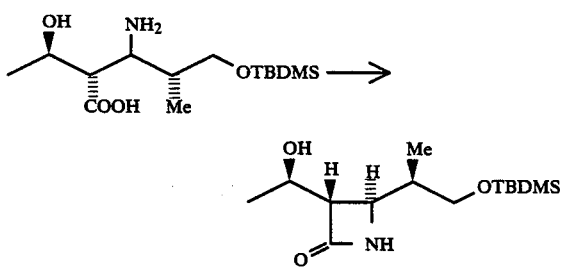

(2S,3R,4R)-3-Amino-5-t-butyldimethylsilyloxy-2-[(1'R)-(1'-hydroxyethyl)]-4-methylpentanoic acid (0.98 g; 3.21 mmol) and 2,2'-dipyridyldisulfide (0.85 g; 3.86 mmol) were dissolved in acetonitrile (300 ml), and a solution of triphenylphosphine (1.01 g; 3.85 mmol) in acetonitrile (62 ml) was added dropwise thereto while heating under reflux. Heating under reflux was continued for 3 hours. After removal of the solvent under reduced pressure, the obtained residue was dissolved in ether (40 ml), washed successively with 1N sodium hydroxide solution (2 ml) three times and a saturated sodium hydrochloride solution (4 ml) two times and dried over anhydrous sodium sulfate. The solvent was distilled under reduced pressure, and the residue was dissolved in ethyl acetate (3.7 ml). Hexane (8.9 ml) was added thereto to crystallize triphenylphosphine oxide, which was removed by filtration. The filtrate was concentrated under reduced pressure to give crude (3S,4S)-3-[(1'R)-1'-hydroxyethyl]-4-[(1'R)-1'-(t-butyldimethylsilyloxymethyl)-ethyl]azetidin-2-one (0.97 g). A portion of the product was purified by TLC using a mixture of hexane and ethyl acetate (2:3) and recrystallized from benzene two times to give colorless needles. M.P., 105°–106° C. [α]$_D^{20}$ −8.6° (c=1.08, CHCl$_3$). [α]$_{405}^{20}$ −31.7° (c=1.08, CHCl$_3$).

IR (KBr): 1089, 1475, 1722, 3230, 3370 cm$^{-1}$.

Mass m/e: 230 (M-t-Bu)[30].

$^1$H NMR δ (CDCl$_3$): 0.09 (6H, s), 0.91 (9H, s), 0.96 (3H, d, J=6.8 Hz), 1.34 (3H, d, J=6.3 Hz), 1.77 (1H, m), 2.83 (1H, bs), 3.03 (1H, dd, J=2.3 and 8.3 Hz), 3.51 (1H, dd, J2.3 and 8.2 Hz), 3.57 (1H, dd, J=6.1 and 10.7 Hz), 3.74 (1H, dd, J=3.9 and 10.6 Hz), 4.08 (1H, bq), 5.90 (1H, bs).

Elementary analysis for C$_{14}$H$_{29}$O$_3$NSi: Calcd.: C, 58.49%; H, 10.17%; N, 4.87%. Found: C, 58.71%; H, 10.00%, N, 4.77%.

Optical purity (determined by $^1$H-NMR using an optically active shifting reagent, i.e. tris[3-(heptafluoropropylhydroxymethylene)-d-camphorato]-europium (III) [Eu(hfc)$_3$]): more than 95% e.e.

REFERENCE EXAMPLE 5-2

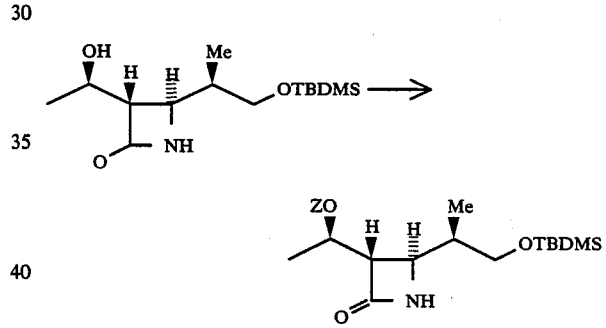

Crude (3S,4R)-3-[(1'R)-1'-hydroxyethyl]-4-[(1'R)-1'-(t-butyldimethylsilyloxymethyl)ethyl]azetidin-2-one (0.160 g; 0.56 mmol) and 4-dimethylaminopyridine (0.133 g; 1.09 mmol) were dissolved in anhydrous dichloromethane (1 ml), and benzyl chloroformate (0.15 ml; 1.05 mmol) was added thereto with ice cooling. The resultant mixture was stirred overnight and concentrated under reduced pressure. Ether (10 ml) was added thereto, and insoluble materials were removed by filtration. The etherial solution was washed successively with water (1 ml) two times and a saturated aqueous sodium chloride solution (1 ml) and dried over anhydrous sodium sulfate. The solvent was distilled under reduced pressure, and the obtained residue was purified by silica gel column chromatography using a mixture of dichloromethane and acetone (99:1) to give (3S,4R)-3-[(1'R)-1'-(benzyloxycarbonyloxy)ethyl]-4-[(1'R)-1'-(t-butyldimethylsilyloxymethyl)ethyl]azetidin-2-one (0.19 g; yield, 85%) as a colorless oil. [α]$_D^{25}$ +10.2° (c=1.10, CHCl$_3$).

IR: 1760 cm$^{-1}$.

Mass m/e: 422 (M+).

$^1$H NMR δ (CDCl$_3$): 0.03 (6H, s), 0.88 (9H, s), 0.95 (3H, d, J=6.8 Hz), 1.44 (3H, d, J=6.4 Hz), 1.50–2.00 (1H, m), 3.15 (1H, bd, 5.15 (2H, s), 7.36 (5H, s).

REFERENCE EXAMPLE 5-3

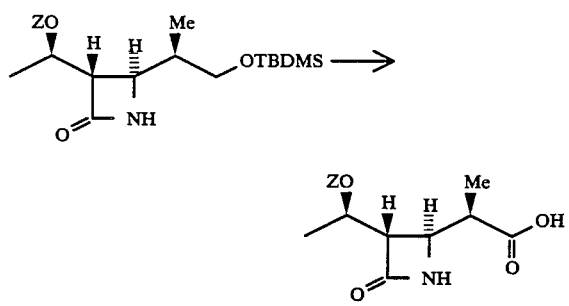

(3S,4R)-3-[(1'R)-1'-(Benzyloxycarbonyloxy)ethyl]-4-[(1'R)-1'-(t-butyldimethylsilyloxymethyl)ethyl]azetidin-2-one (110 mg) was dissolved in acetone (1 ml), and a Jones' oxidizing agent was added dropwise thereto at room temperature. Dropwise addition was continued until the reaction mixture remained unchanged for more than 30 minutes. The reaction mixture was treated with isopropanol to inactivate excess of the oxidizing agent and passed through a silica gel short column to remove inorganic salts, whereby there was obtained (3S,4R)-3-[(1'R)-1'-(benzyloxycarbonyloxy)ethyl]-4-[(1'R)-1'-carboxyethyl]azetidin-2-one (86.2 mg; quantitative yield). Recrystallization from a mixture of carbon tetrachloride and dichloromethane gave the purified product. M.P., 112°–114° C. $[\alpha]_D^{25}$ +6.5° (c=1.05, CHCl$_3$).

IR (KBr): 1755, 1730, 1675 cm$^{-1}$.

Mass m/e: 321 (M$^{30}$).

$^1$H NMR δ (CDCl$_3$): 1.20 (3H, d, J=7.0 Hz), 1.40 (3H, d, J=6.4 Hz), 2.66 (1H, dq, J=6.8 Hz), 3.19 (1H, dd, J=1.6 and 7.6 Hz), 3.83 (1H, dd, J=2.2 and 5.7 Hz), 5.14 (2H, s), 6.42 (1H, bs), 7.34 (5H, s).

REFERENCE EXAMPLE 5-4

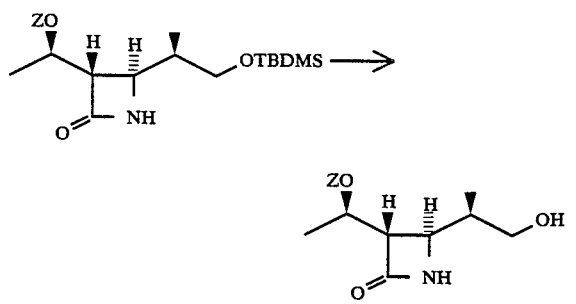

(3S,4R)-3-[(1'R)-1'-(Benzyloxycarbonyloxy)ethyl]-4-[(1'R)-1'-(t-butyldimethylsilyloxymethyl)ethyl]azetidin-2-one (26.4 mg; 0.063 mmol) was dissolved in a mixture of acetic acid (0.4 ml), tetrahydrofuran (0.2 ml) and water (0.1 ml), and the resultant mixture was stirred at 70° C, for 3 hours. After removal of the solvent, the residue was purified by silica gel column chromatography using a mixture of hexane and ethyl acetate (4:6–0:10) to give (3S,4R)-3-[(1'R)-1'-(benzyloxycarbonyloxy)ethyl]-4-[(1'R)-1'-(hydroxymethyl)ethyl]azetidin-2-one (12.5 mg; yield, 65%). $[\alpha]_D^{25}$ +10.1° (c=1.26, CHCl$_3$).

IR (neat): 1743 cm$^{-1}$.

Mass m/e: 307 (M+).

$^1$H NMR δ (CDCl$_3$): 0.94 (3H, d, J=7 Hz), 1.46 (3H, d, J=6 Hz), 3.19 (1H, dd, J=9 and 1 Hz), 5.07 (2H, s), 6.10 (1H, bs), 7.35 (5H, s).

REFERENCE EXAMPLE 5-5

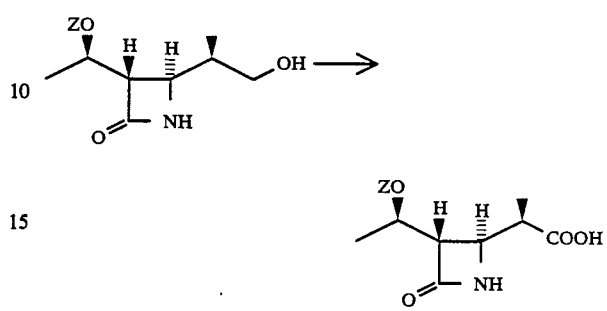

(3S,4R)-3-[(1'R)-1'-(Benzyloxycarbonyloxy)ethyl]-4-[(1'R)-1'-(hydroxymethyl)ethyl]azetidin-2-one (52.5 mg; 0.17 mmol) was dissolved in acetone (1 ml), and a Jones' oxidizing agent was added dropwise thereto at room temperature. Dropwise addition was continued until the reaction mixture remained unchanged, and the reaction mixture was passed through a silica gel short column to remove inorganic salts, whereby there was obtained (3S,4R)-3-[(1'R)-1'-(benzyloxycarbonyloxy)ethyl]-4-[(1'R)-1'-carboxyethyl]azetidin-2-one (52.3 mg; yield, 95%). Recrystallization from a mixture of hexane, ethyl acetate and acetic acid (3:7:0.01) gave the purified product. Its melting point, specific optical rotation and IR, NMR and Mass spectra were identical to those of the product as obtained in Reference Example 5-3.

What is claimed is:

1. An amino acid compound of the formula:

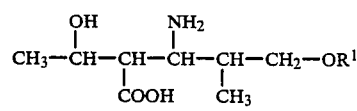

wherein R$^1$ is a protective group.

2. The amino acid compound according to claim 1, having the formula:

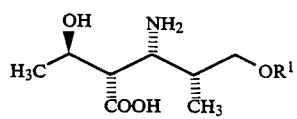

wherein R$^1$ is a hydroxyl-protected group.

3. A process for preparing an amino acid compound of the formula:

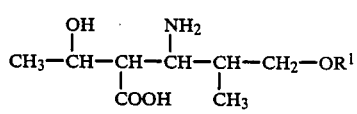

wherein R$^1$ is a hydroxyl-protective group, which comprises subjecting an oxazolidine compound of the formula:

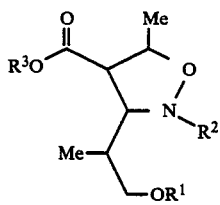

wherein R² is an amino-protective group and R³ is a hydrogen atom or a carboxyl-protective group and R¹ as defined above, to cleavage by catalytic hydrogenation of the nitrogen-oxygen bond and then subjecting the resultant product to elimination of the amino-protective group and the carboxyl-protective group by catalytic hydrogenation or, contacting with an acid or alkali.

4. A process for preparing an amino acid compound of the formula:

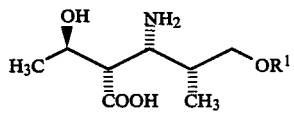

wherein R¹ is a hydroxyl-protective group, which comprises subjecting a mixture of the diastereomers of an oxazolidine compound of the formula:

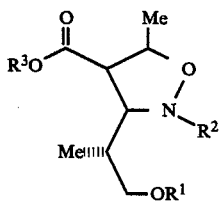

wherein R² is an amino-protective group and R³ is a hydrogen atom or a carboxyl-protective group and R¹ is as defined above to selectively hydrolyze the 3,4-trans-diastereomers with a selective hydrolyzing agent, recoving the non-hydrolyzed 3,4-cisdiastereomers of the formulas:

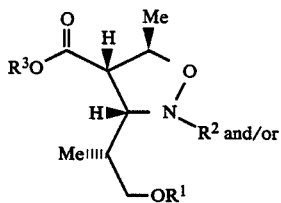

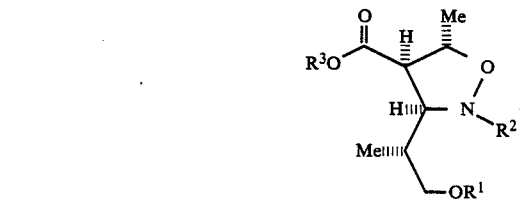

wherein R¹, R² and R³ are each as defined above from the reaction mixture, hydrogenating the thus recovered 3,4-cisdiastereomers to cleave the nitrogen-oxygen bond catalytic hydrogenation and then eliminating the amino-protective group and and the carboxyl-protective group from the resultant product by catalytic hydrogenation or, contacting with an acid or alkali.

5. A process according to claim 4 wherein said selective hydrolyzing agent is selected from the group consisting of barium hydroxide, sodium hydroxide, potassium hydroxide, and tetrabutyl ammonium hydroxide.

6. The amino acid compound according to claim 2, wherein R¹ is a tri(lower)alkylsilyl group or a tetrahydropyranyl group.

7. The amino acid compound according to claim 2, wherein R¹ is t-butyldimethylsilyl or tetrahydropyranyl.

* * * * *